(12) United States Patent
Gebhardt et al.

(10) Patent No.: US 7,001,390 B2
(45) Date of Patent: Feb. 21, 2006

(54) ANCHORING ELEMENT FOR ANCHORING A LIGAMENT TRANSPLANT

(75) Inventors: Ullrich Gebhardt, Bautzen (DE); André Timmermans, Ruurlo (NL)

(73) Assignee: Karl Storz GmbH & Co. KG, (DE)

( * ) Notice: Subject to any disclaimer, the term of this patent is extended or adjusted under 35 U.S.C. 154(b) by 329 days.

(21) Appl. No.: 10/361,741

(22) Filed: Feb. 10, 2003
(Under 37 CFR 1.47)

(65) Prior Publication Data
US 2005/0004670 A1    Jan. 6, 2005

(30) Foreign Application Priority Data
Feb. 8, 2002    (EP) .................................. 02002861

(51) Int. Cl.
*A61B 17/56* (2006.01)
(52) U.S. Cl. ...................................... 606/72; 623/13.14
(58) Field of Classification Search ................ 606/72, 606/88, 151, 232; 623/13.14, 13.13, 13.15, 623/13.17
See application file for complete search history.

(56) References Cited

U.S. PATENT DOCUMENTS

| 4,755,184 | A | * | 7/1988 | Silverberg ............... 623/23.56 |
| 5,501,706 | A |   | 3/1996 | Arenberg ..................... 623/16 |
| 5,899,938 | A | * | 5/1999 | Sklar et al. ............. 623/13.14 |
| 6,267,767 | B1 | * | 7/2001 | Strobel et al. ............. 606/104 |
| 6,746,483 | B1 | * | 6/2004 | Bojarski et al. ......... 623/13.14 |

FOREIGN PATENT DOCUMENTS

| DE | 198 51 152 | 5/2000 |
| EP | 0 642 773 | 3/1995 |
| WO | WO 93/15694 | 8/1993 |
| WO | WO 98/37835 | 9/1998 |
| WO | WO 99/44544 | 9/1999 |
| WO | WO 01/82989 | 11/2001 |

* cited by examiner

Primary Examiner—Pedro Philogene
(74) Attorney, Agent, or Firm—St. Onge Steward Johnston & Reens LLC

(57) ABSTRACT

An anchoring element serves for anchoring a ligament transplant in a channel in a bone. The anchoring element has a body which can be brought into an intermediate space between an inner wall of a channel within a bone and a ligament transplant introduced into the channel. The body serves for clamping the ligament transplant in the channel. The body has an outer flexible sheath filled with particles which are of low compressibility, the particles within the outer flexible sheath allowing the outer flexible sheath to accommodate to a shape of the intermediate space between the ligament and the channel (FIG. 4).

12 Claims, 3 Drawing Sheets

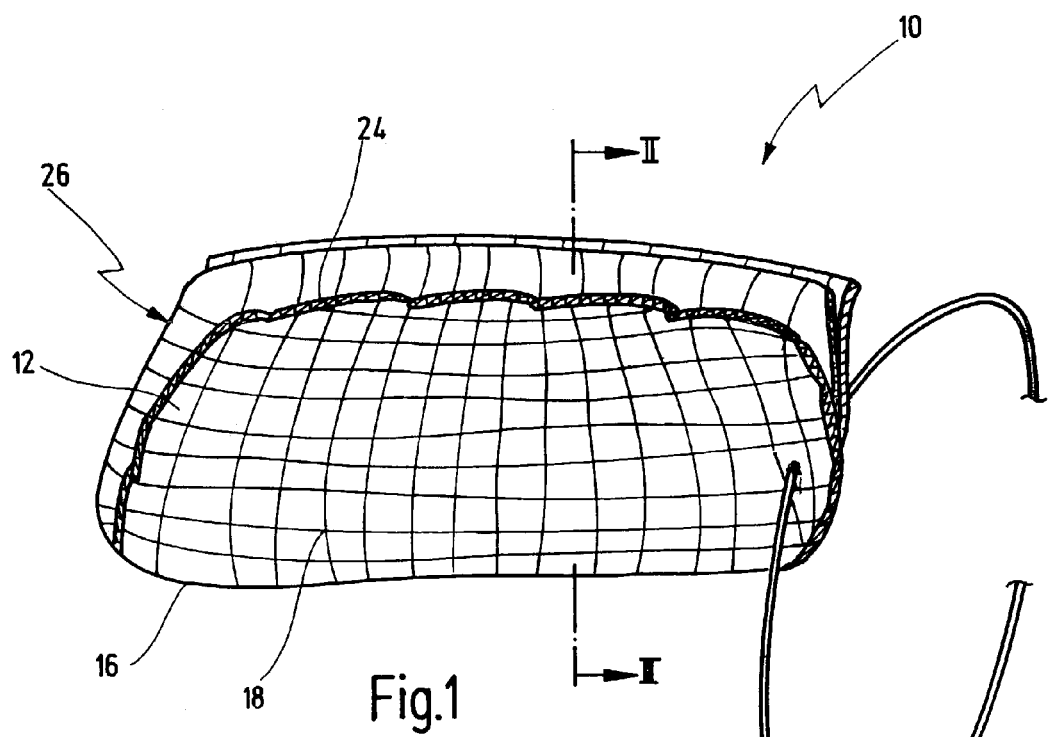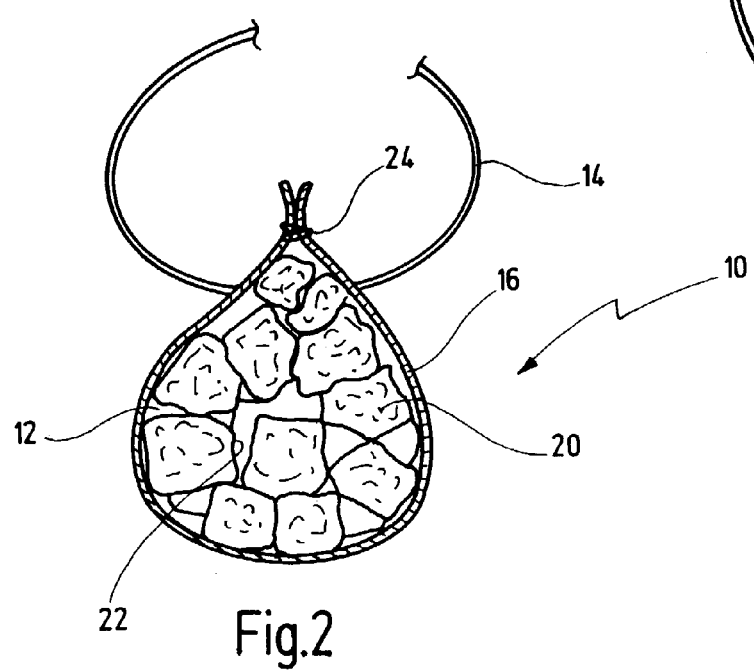

ANCHORING ELEMENT FOR ANCHORING A LIGAMENT TRANSPLANT

This application claims priority from pending European Patent Application No. 02 002 861.9 filed on Feb. 8, 2002.

FIELD OF THE INVENTION

The invention relates to an anchoring element for anchoring a ligament transplant in a channel in a bone, with a body which can be brought into an intermediate space between an inner wall of the channel and the outer side of the ligament transplant introduced therein and, as a result, clamps the ligament transplant in the channel.

An anchoring element of this type is known for example from German Patent Application 198 51 152.

Anchoring elements of this type are used in operations in which a damaged ligament is replaced by a ligament transplant.

A typical case is, for example, a cruciate ligament replacement in a knee joint.

Such operations are required if the cruciate ligament in the knee is torn or badly damaged in some other way.

In this case, materials taken from the same body are preferred for use as the cruciate ligament replacement. The patellar tendon or the semitendinosus tendons have proven in particular to be suitable for producing the required cruciate ligament replacement.

This surgical technique is to be explained by way of example in the case of the replacement of a cruciate ligament on a knee joint. This technique may also be applied to other joints, for example the shoulder joint, or else other parts of the body in which bones are joined to one another by means of ligaments.

In the case of the method described in the publication cited at the beginning, the semitendinosus tendon is used as a cruciate ligament replacement. It is removed from the patient with the aid of a tendon cutter and subsequently divided up into individual segments or portions. Some of these segments are placed together in the form of a loop, creating double-stranded segments. These individual segments or else the double strands are subsequently placed alongside one another and joined to one another at their ends by suture threads. If two double strands are joined to each other, this is referred to as a quadruple technique. The tendon cluster produced in this way forms the cruciate ligament replacement that is the ligament transplant.

In the case of a cruciate ligament replacement, the transplant is fastened between the distal end of the femur and the proximal end of the tibia. For this purpose, firstly a through-hole is drilled in the proximal end of the tibia and a blind-hole is drilled in the distal end of the femur. A respective end of the cruciate ligament replacement is inserted into these two holes and fixed in the holes.

The drilled channel has a circular cross section. If a ligament transplant in the form of a double strand is inserted into such a drilled channel, its cross section has approximately the shape of an "8". Accordingly, an intermediate space is produced between the inner wall of the drilled channel and the outer side of the ligament transplant introduced into it, which in the example of a cruciate ligament replacement in the form of a double strand has on each side a cross section approximately in the form of a double sickle.

For fixing the ligament transplant in, the channel, anchoring elements are then provided and are driven into the intermediate space between the inner wall of the drilled channel and the outer side of the ligament transplant.

In the case of DE 198 51 152, cited at the beginning, the anchoring elements take the form of cylindrical plugs. These cylindrical plugs consist of a compacted and consequently non-plastic bone material, and they are of such a size that they act as clamping pieces between the outer side of the double strand of the tendon transplant and the inner wall of the drilled channel. The cylindrical plugs are in contact with the transplant, in particular in the region of the constriction of the "8" of the double strand, on the opposite side with a certain peripheral region against the inner side of the circular channel wall. The plugs of compressed bone material are not plastically deformable and their hardness is greater than that of the tendon material, so that the tendon is squeezed somewhat by deformation.

The disadvantage of this is that impairment of the tendons may be caused as a result, which may lead to ruptures when they are subjected to loads, in particular the considerable loads in the knee joint.

If there is incongruence between the drilled channel and the transplant, the tendon oscillates in the channel and also undergoes a rotary motion in the channel during the final rotation of the joint. The transplant does not heal in the spongy drilled channel, and is held only by the suspension and by scar tissue. The continuing instability leads to a high intra-articular pressure, with constant pressing of synovial fluid into the drilled channels, resulting in increased instability damage.

The oscillating back and forth of the tendon replacement in the drilled channel causes the channel to widen in a flared manner towards the outer side, this being further exacerbated by hard pin-like anchoring elements, so that the phenomenon known by the technical term "windscreen wiper effect" occurs.

Various efforts have now been undertaken to counteract this phenomenon.

It is known from U.S. Pat. No. 6,001,101 to provide hard rigid anchoring elements which fill as large an area as possible of the intermediate space between the inner wall of the drilled channel and the outer side of the ligament transplant with positive engagement.

In this case there is the problem that the size and shape of the ligament transplant is dependent on numerous factors, that is for example the age and stature of the patient, and on the technique applied, that is a single-strand technique, a double-strand technique or a quadruple-strand technique.

This necessitates a large number of rigid anchoring elements of different sizes and different shapes. Even then, the problem of the "windscreen wiper effect" may not be overcome, since the hard and solid anchoring elements of an adapted shape would in fact transfer this oscillating motion to the bone wall surrounding the drilled channel and it is not possible to rule out the chance of a clearance nevertheless gradually occurring, or the undesired flared widening of the mouth of the channel.

In the case of other approaches to a solution, it is attempted to anchor the tendon or fix it in the drilled channel by what are known as fixation screws.

U.S. Pat. No. 5,961,521 discloses the combined use of anchoring elements in a specific adapted shape together with a fixation screw.

This solution not only has the disadvantage that numerous components are necessary, it is also not possible to rule out the chance of the tendon being impaired by the combination of the anchoring element and fixing screw.

This surgical technique is always faced with the requirement of providing a secure and physiological anchorage of the transplant that is to be carried out as atraumatically and pleasantly as possible for the patient. The aim is to achieve rapid inward growth of the ligament transplant, which after all is an organ product of the patient. Interference screws for fixing, for example made of metallic materials, are foreign bodies which first have to be removed from the body in the event of later modifications.

With hard anchoring elements there is the risk of the anchorage developing excessive clamping force and therefore no longer being atraumatic.

It is therefore an object of the present invention to provide an anchoring element which enables a secure and an atraumatic anchoring of the ligament transplant together with a with long-term stability of anchoring. In addition, it is intended that one type of anchoring element can be used for different surgical techniques, i.e. for different forms of tendon transplants.

SUMMARY OF THE INVENTION

This object is achieved by a body having an outer flexible sheath filled with particles which are of low compressibility, said particles within said outer flexible sheath allowing the body to accommodate to a shape of said intermediate space between said ligament and said channel.

Due to the flexibility of the outer flexible sheath and the particulate material contained therein, the body is deformable to a certain extent, which means allowing a certain deformation to adapt to the respective space. The individual particles within the outer flexible sheath allow this deformation to a certain extent. But, due to the low compressibility of the particles, the deformed or adapted body can nevertheless exert clamping forces onto the tendon to be clamped within the channel of the bone. The outer flexible sheath prevents that the body loses its entire shape; it allows only a deformation within the surface defined by the outer flexible sheath.

If, for example, a single-strand tendon of an approximately rectangular cross section, for example the patellar tendon, is introduced into a drilled channel of a round cross section, the plastically deformable body adapts itself to the corresponding geometry of the intermediate space. The same anchoring element can also be inserted, however, into an intermediate space which is produced on one side between a round drilled channel and a double-stranded transplant. The same is possible in the case of a strand which has been produced by the quadruple technique. It has been found that the adaptation of the body to the intermediate space does not cause loosening to take place, since the snugly fitting body is in contact over a large surface area both with the inner wall of the drilled channel and with the outer side of the tendon implant. In contrast with interference screws, which are difficult to introduce, the risk of traumatization of the cartilage and bone are much lower. Likewise, the "windscreen wiper effect" has no longer being observed. This can be explained by the fact that the complete filling of the drilled channel cross section by the tendon material on the one hand and the deformable body of the anchoring element on the other hand produces a compact, locationally fixed composite composition which provides an atraumatic anchorage, but nevertheless allows certain movements when the tendon transplant is subjected to loading, without leading to loosening effects.

The flexible sheath makes the deformation possible, but on account of the sheath the material is held within this sheath, so that quite definite retaining or anchoring points are created in a certain delimited region, for example not over an entire length of a drilled channel but only over a specific region, for example in the end region of a drilled channel.

The particles itself can be very hard and the plastic deformability is produced by the desired shapes being able to form on the basis of the divided nature of the material in the sheath. This can be imagined as resembling a filled bag of sand which can be correspondingly deformed, but can withstand sudden compressive loads, such as for example moving of a tendon.

In a further design of the invention, the sheath has a perforated structure.

This measure has the advantage that bone material can grow into the body via the perforated structure, so that a solid bond is then produced between the body and the bone surrounding it.

In a further design of the invention, the material of the sheath is biodegradable.

This measure has the advantage that the sheath is gradually biodegraded and the material present in the sheath is three-dimensionally grown through by a bone matrix.

In a further design of the invention, the plastically deformable material is biodegradable.

This measure has the advantage that the material is gradually biodegraded after it has grown three-dimensionally together with the bone, and can then be replaced by further growth of the bone material.

In a further design of the invention, the plastically deformable material is formed as divided bone material.

This measure has the considerable advantage that particularly favorable integration of the anchorage body can take place. If the divided bone material is material taken from the same patient, this already provides the body's own bone materials, into which material of the same body can grow without any problem and grow together with this divided bone material.

For this purpose, the bone material which was previously removed in the region of the drilled channel may be used, for example by finely divided comminution of this bone material.

For this purpose, the sheath may initially be formed as an open sheath, into which the bone material can be filled and which is subsequently closed, for example by sewing. The sheath is thus formed almost as a quill into which the finely divided bone material of the patient is filled. The perforated structure of the sheath has the considerable advantage in this connection that "hemorrhaging" can take place from the surroundings through the mesh and consequently an integration of the "foreign body" can take place particularly rapidly.

In a further design of the invention, the body is joined to a pulling thread.

This measure has the considerable advantage that the handling, introduction and positioning of the body is facilitated.

In a further design of the invention, the body originally has an approximately cylindrical shape.

This measure has the considerable advantage that this shape facilitates introduction or pulling into the intermediate space, after which the body is formed plastically into the respectively existing shape of the intermediate space by corresponding manipulations.

In a further design of the invention, the body originally has an approximately frustoconical shape.

This measure has the advantage that a simple attachment of the, anchoring element to the intermediate space is provided by means of the thinner end.

The body may in this case either be prefabricated, depending on design and materials, or it may be fabricated shortly before the operation. For this purpose, the sheath is, for example, designed as a quill or merely as a rectangular formation, to which the bone material is applied in divided form, for example as small cubes, and this mesh is subsequently closed, for example sewn, to form a closed body.

It goes without saying that the features stated above and still to be explained below can be used not only in the combination respectively specified but also in other combinations or on their own without departing from the scope of the present invention.

BRIEF DESCRIPTION OF DRAWINGS

The invention is described in more detail and explained below on the basis of several selected exemplary embodiments in conjunction with the accompanying drawings, in which:

FIG. 1 shows a side view of an anchoring element according to the invention in the form of a sewn quill comprising a mesh structure, which is joined to a pulling thread and is filled with small cubes of spongiosa, FIG. 2 shows a cross section through the anchoring element from FIG. 1, along the line II—II.

DETAILED DESCRIPTION OF DRAWINGS

Figure 3:
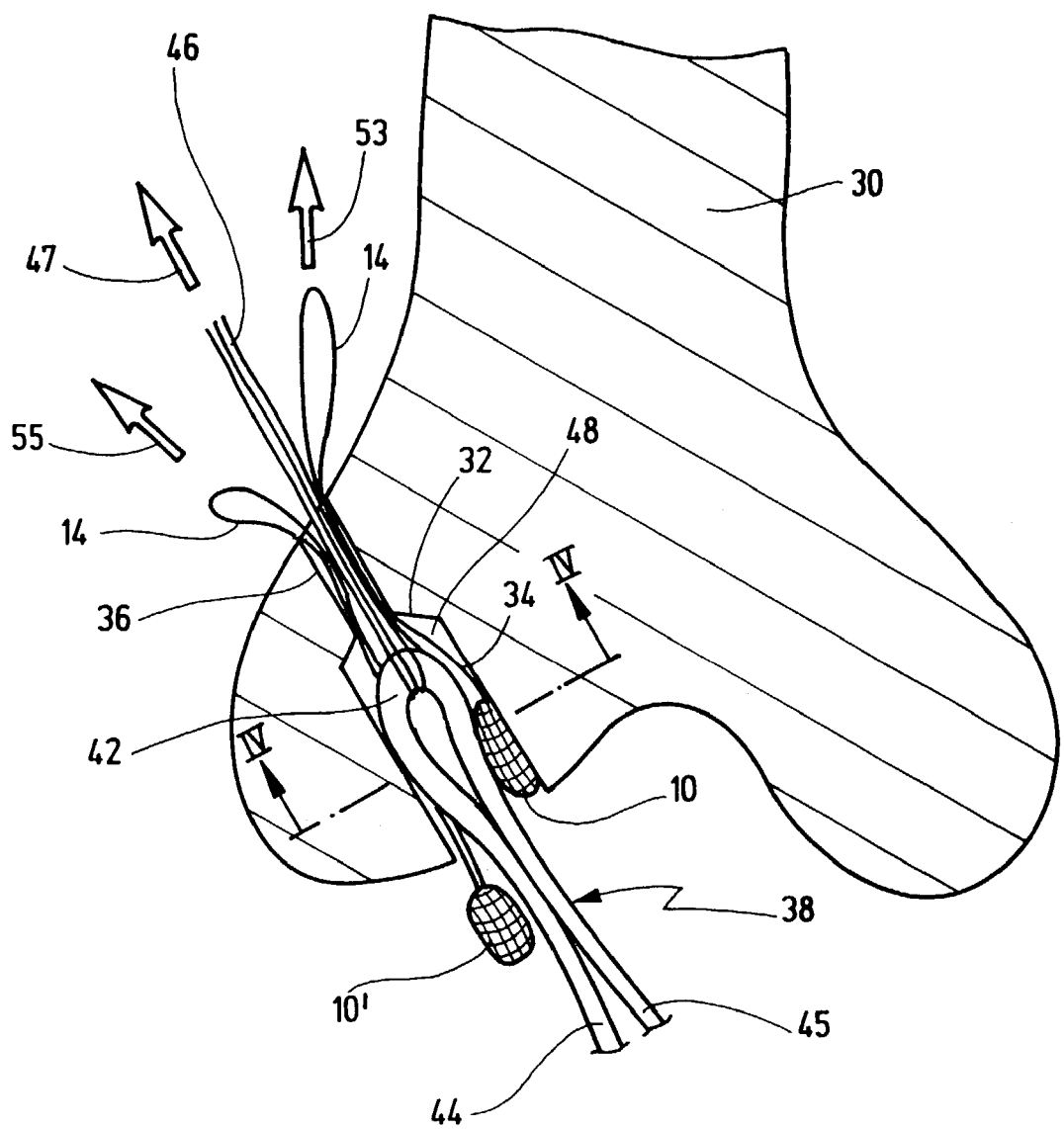
FIG. 3 shows in a greatly schematized form a longitudinal section through a femur in which a ligament transplant is being inserted, with the aid of anchoring elements according to the invention.

An anchoring element according to the invention, represented in FIGS. 1 and 2, is provided overall with the reference numeral 10.

The anchoring element 10 has a roughly rod-shaped or cylindrical body 12, which is joined to a pulling thread 14.

The outer side of the body 12 is closed off by a sheath 16, which has a mesh-like structure 18. Mesh-like means that there are numerous openings in the sheath 16, making it possible for example for a fluid to penetrate from the outside into the space inside the sheath 16. Accommodated in the sheath 16 is a material 20 in the form of numerous particles in the form of cubes 22 of spongiosa. The cubes do not have to have the exact form of a cube and are approximately 0.5–3 mm in size.

In the unwound state, the sheath 16 has an approximately rectangular shape and a quantity of the cubes 22 were placed approximately centrally onto this shape. The cubes 22 may result from a drilling process for preparing a bore channel in a bone, i.e. the femur 30 shown in FIG. 3. The core of bone material drilled out is divided into the cubes 22. Subsequently, two opposite sides were folded over and placed against each other and the body sewn by means of an approximately U-shaped seam 24 to form a closed body 12 or quill. Accordingly, the sheath 16 encloses the plastically deformable mass of cubes 22 of spongiosa accommodated therein. The sheath 16 is, furthermore, joined to a pulling thread 14, which has simply been inserted through the body 12 by piercing with a needle. Depending on the configuration, the pulling thread 14 is tied together at its outer ends, consequently joined to form a loop.

Use of the anchoring elements according to the invention is to be described in more detail below by way of example on the basis of FIGS. 3 to 5, a cruciate ligament replacement in a knee joint being taken here by way of example.

In FIG. 3, only the femur of the knee joint is represented. The ligament transplant 38 indicated there in the form of a cruciate ligament replacement also extends as far as the tibia, as known per se in the case of this surgical technique.

A continuous channel 32, which has a first portion 34 of a larger diameter which is followed by a second portion 36 of a smaller diameter, has been drilled into the femur in an outwardly inclined manner, from the side of the joint.

The second portion 36 opens out on the outer side of the femur, the first portion 34 opens out in the region of the joint. The ligament transplant 38 used comprises a semitendinosus tendon, which has been placed in such a way as to produce two strands 44 and 45 running alongside each other, which are joined together via a loop 42.

In the region of the loop 42, this cruciate ligament replacement is pulled into the first portion 34 of larger diameter of the channel 32. For this purpose, the loop 42 is joined to a number of threads 46, which were previously threaded through the channel 32.

As represented in FIG. 3 by an arrow 47, the surgeon can pull on the corresponding threads 46 and thereby pull the loop 42 into the channel and position it.

Equally, a first anchoring element 10 has already been pulled into the first portion 34 of larger diameter, its pulling thread 14 likewise having been threaded through the channel 32 in advance and protruding out via the mouth of the second portion 36 of smaller diameter. By pulling on the pulling thread 14, as indicated in FIG. 3 by an arrow 53, the body of the anchoring element 10 can be brought into the intermediate space 48 between the inner wall 50 of the portion 34 of larger diameter and the outer side 52 of the ligament transplant 38, as can be seen in FIG. 4 at the upper end. On account of the plastic deformability, the body 12 of the anchoring element 10 assumes the shape of this intermediate space 48, that is approximately the shape of a double sickle.

In FIG. 3, the ligament transplant 38 is indicated as twisted somewhat, in order to show its double-stranded nature. After the ligament transplant 38 has been pulled in, the second anchoring element 10' can then also be pulled in, by pulling on its pulling thread 14', which has likewise been threaded through the channel 32 in advance, as indicated in FIG. 3 by the arrow 55.

Figure 4:
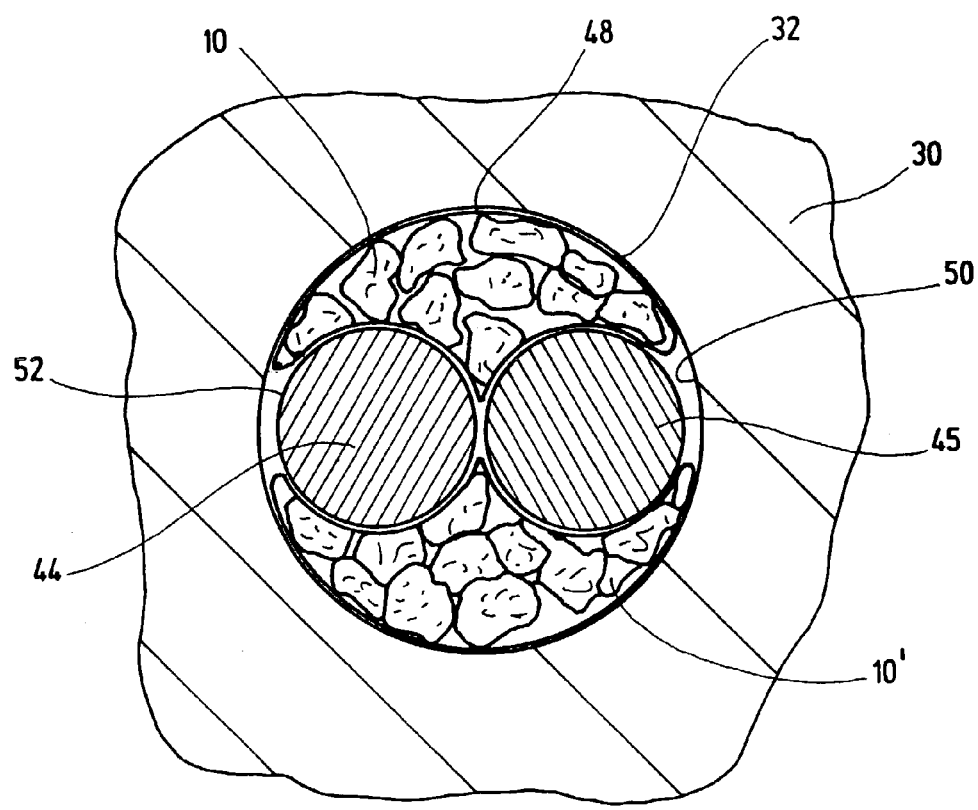
FIG. 4 shows a greatly enlarged cross section along the line IV—IV in FIG. 3 after anchoring the ligament transplant.

As can be seen in particular from the sectional representation of FIG. 4, the anchoring elements 10, 10' almost completely fill the intermediate space 48 present on both sides of the double-stranded ligament transplant 38, so that an exact anchored fit is created.

A surgical technique in which anchoring elements 10 and 10' have respectively been inserted on either side of the double-stranded ligament transplant 38 has been described.

It is also conceivable to place the double strand on one side and to introduce only one anchoring element for anchoring.

It can be seen in particular from the sectional representation from FIG. 4 that, when the transplant 38 moves back and forth, for example upwards or downwards in the representation of FIG. 4, no flared widening of the channel 32 takes place, since such forces can be damped by the plastic mass of the cubes of spongiosa.

The fact that the sheath 16 has a perforated structure 18 means that it is possible for appropriate fluids that promote the growth of corresponding osteoblasts to enter, so that intimate growing together of the transplant 38 and the bone 30 can take place as soon as possible in the region of the anchoring elements 10 and 10'.

The entire space inside the channel, is filled by substances taken from the same patient, that is by the patient's own semitendinosus tendon and own spongiosa cubes, so that a particularly favorable inward growth is possible without reactions of rejection. If a bioresorbable material is used for the sheath 16, for example a biodegradable VICRYL mesh, this is biodegraded as soon as possible, so that only materials taken from the same body are present.

The pulling threads 14, 14' of the anchoring elements 10 and 10' not only facilitate handling when introducing or pulling in the anchoring elements 10, 10' but also provide fixing, at least until the respective anchoring element 10, 10' has grown in.

Figure 5:
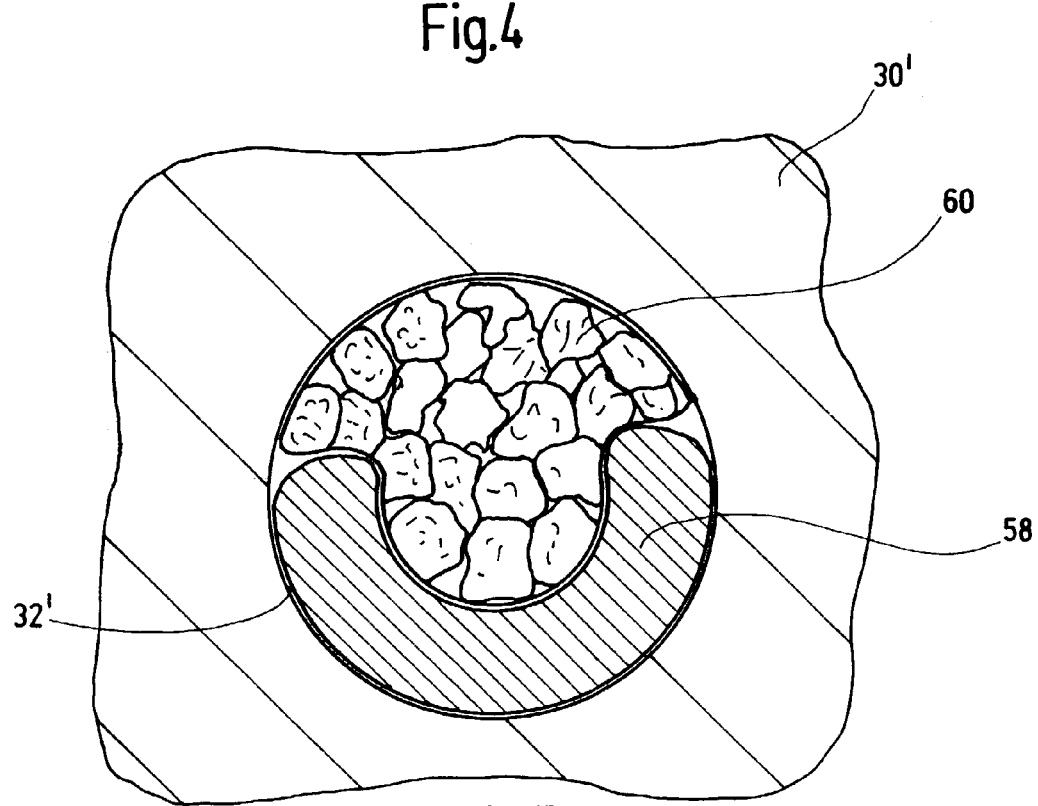
FIG. 5 shows a representation comparable to the section of FIG. 4 when a differently shaped ligament transplant is used.

In the case of the exemplary embodiment represented in FIG. 5, an appropriate circular channel 32' has equally been drilled into a bone 30' and a ligament transplant 58, which originally has a somewhat elongate rectangular cross section, for example a patellar tendon taken from the same body, has been inserted. The corresponding anchoring element 60 is formed like the anchoring elements 10, 10' and can then fill the corresponding intermediate space between the channel 32' and the ligament implant 58 on account of its plastic deformability, as can be seen from the sectional representation.

Since, once all the materials taken from the same body have grown in and, if appropriate, the corresponding sheath has biodegraded, the operating site can no longer be seen from the outside, for example by X-ray examinations, corresponding markers may be introduced into the anchoring elements for monitoring purposes, whether in the mesh or between the cubes of spongy material, in order to allow the actual operating site nevertheless to be radiologically picked up. The surgical techniques described above were described in conjunction with a cruciate ligament replacement, but may equally be used also in the case of other surgical techniques for other joints, whether in the shoulder joint, in the ankle joint or other joints.

What is claimed is:

1. Anchoring element for anchoring a ligament transplant in a channel in a bone, comprising
   a body which can be brought into an intermediate space between an inner wall of a channel within a bone and a ligament transplant introduced into said channel, said body serves for clamping said ligament transplant within said channel, wherein
   said body has an outer flexible sheath filled with a plurality of particles having a low compressibility, said particles within said outer flexible sheath allowing said body to accommodate to a shape of said intermediate space between said ligament and said channel.

2. The anchoring element of claim 1, wherein said outer flexible sheath has a perforated structure.

3. The anchoring element of claim 1, wherein said outer flexible sheath is made of a material which is biodegradable.

4. The anchoring element of claim 1, wherein said individual particles within said outer flexible sheath are biodegradable.

5. The anchoring element of claim 1, wherein said individual particles are divided bone particles.

6. The anchoring element of claim 1, wherein said body is joined to a pulling thread.

7. The anchoring element of claim 1, wherein said body originally has an approximately cylindrical shape.

8. The anchoring element of claim 1, wherein said body originally has an approximately frustoconical shape.

9. A method for anchoring a ligament transplant in a channel in a bone, with an anchoring element comprising the steps of
   providing a channel within a bone,
   inserting into said channel a ligament transplant having a diameter smaller than a diameter of said channel,
   introducing an anchoring element into an intermediate space between said ligament and said channel for clamping said ligament transplant, said method comprising the steps of
   providing an anchoring element having an outer flexible sheath filled with individual particles which are of low compressibility,
   accommodating a shape of said deformable anchoring element to a shape of said intermediate space between said ligament and said channel when inserted into said intermediate shape.

10. The method of claim 9, comprising the following additional steps
    providing said outer flexible sheath in an open form,
    filling said open form flexible sheath with particles of bone material, and
    closing said outer flexible sheath.

11. The method of claim 10, wherein said filling of said flexible sheath is performed with particles of bone material taken from the human being at which said ligament transplant has to be anchored via said anchoring element.

12. The method of claim 11, wherein said bone material taken from said human being is a bone material resulting from a drilling process for preparing said channel within said bone, in which said transplant is anchored.

* * * * *